United States Patent [19]

Buchecker et al.

[11] Patent Number: 5,372,746
[45] Date of Patent: Dec. 13, 1994

[54] FLUORO-SUBSTITUTED TOLANE COMPOUNDS AND LIQUID CRYSTALLINE MIXTURES CONTAINING SAME

[75] Inventors: Richard Buchecker, Zurich; Martin Schadt, Seltisberg, both of Switzerland

[73] Assignee: Hoffmann-La Roche Inc., Nutley, N.J.

[21] Appl. No.: 977,367

[22] Filed: Nov. 17, 1992

[30] Foreign Application Priority Data

Nov. 19, 1991 [CH] Switzerland ............... 3375/91
Jun. 18, 1992 [CH] Switzerland ............... 1918/92

[51] Int. Cl.$^5$ ............... C09K 19/34; C07D 319/06
[52] U.S. Cl. ............... 252/299.61; 549/369; 549/374
[58] Field of Search ........... 252/299.1, 299.61, 299.63, 252/299.64, 299.65, 299.66, 299.67; 549/369, 374

[56] References Cited

U.S. PATENT DOCUMENTS 5,194,178  3/1993  Coates et al. ............... 252/299.63

FOREIGN PATENT DOCUMENTS 3909802  3/1989  Germany .
4000535  10/1990  Germany .
4105742  2/1991  Germany .
4111990  4/1991  Germany .
2240544  7/1991  United Kingdom .

OTHER PUBLICATIONS

Derwent Abstract E14 L03 U11 V07 (E13) (1990) for DE-4000535.
Derwent Abstract E19 L03 U11 V07 (1988) for DE-3909802.
Derwent Abstract E14 L03 U11 V07 (1991) for DE-4111990.
Derwent Abstract E14 L03 (1991) for DE-4105742.

*Primary Examiner*—Shean Wu
*Attorney, Agent, or Firm*—George M. Gould; William H. Epstein; Catherine R. Roseman

[57] ABSTRACT

Compounds of the general formula

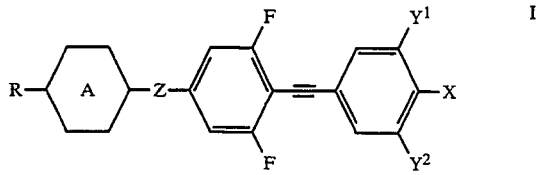

wherein
ring A represents 1,4-phenylene, pyridine-2,5-diyl, pyrimidine-2,5-diyl, trans-1,4-cyclohexylene or trans-1,3-dioxane-2,5-diyl;
Z signifies a single covalent bond, —CH$_2$CH$_2$—, —OCH$_2$—, —CH$_2$O—, —(CH$_2$)$_4$—, —O(CH$_2$)$_3$—, —(CH$_2$)$_3$O— or, where ring A represents a saturated ring, also the trans form of —CH=CH(CH$_2$)$_2$— or —CH=CHCH$_2$O—;
X signifies fluorine, chlorine, cyano, —CF$_3$, —OCF$_3$ or —OCHF$_2$;
Y$^1$, Y$^2$ each independently signify fluorine or hydrogen; and
R signifies alkyl, alkoxy, alkenyl or alkenyloxy with 1 or, respectively, 2 to 12 carbon atoms in which one CH$_2$ group or two non-adjacent CH$_2$ groups can be replaced by oxygen and/or one or more hydrogen atoms can be replaced by fluorine atoms, their manufacture, liquid crystalline mixtures which contain such compounds, as well as the use of these compounds and mixtures for electro-optical purposes.

7 Claims, No Drawings

FLUORO-SUBSTITUTED TOLANE COMPOUNDS AND LIQUID CRYSTALLINE MIXTURES CONTAINING SAME

FIELD OF THE INVENTION

The present invention is concerned with novel compounds having a poly-fluorinated tolane structure, their manufacture, liquid crystalline mixtures which contain such compounds as well as the use of these compounds or mixtures for electro-optical purposes.

BACKGROUND OF THE INVENTION

Liquid crystals are used primarily its dielectrics in indicating devices, since the optical properties of such substances can be influenced by an applied voltage. Electro-optical devices based on liquid crystals are well-known to a person skilled in the art and can be based on various effects. Such devices are, for example, cells having dynamic scattering, DAP cells (deformation of aligned phases), guest/host cells, TN cells having a twisted nematic structure, STN cells ("super twisted nematic"), SBE cells ("super birefringence effect") and OMI cells ("optical mode interference"). For displays having a high content of information multiplexed, especially the actively controlled, e.g. TFT cells ("thin film transistor"), have recently become important besides the passively controlled. The most common indicating devices are based on the Schadt-Helfrich effect and have a twisted nematic structure.

The liquid crystal materials must have a good chemical, photochemical and thermal stability and must have a good stability towards electric fields. Further, they should have a suitable mesophase over a range which is as broad as possible (for example a nematic or a cholesteric phase for the cells mentioned above), but nevertheless should have a sufficiently low viscosity and in the cells should permit short response times, low threshold potentials and a high contrast. Further properties such as the electrical conductivity, the dielectric anisotropy and the optical anisotropy must fulfil different requirements depending on the field of use and type of cell. For example, materials for cells having a twisted nematic structure should have a positive dielectric anisotropy which is as high as possible and at the same time should have a conductivity which is as low as possible. This latter property is above all of particular importance for TFT cells. Unfortunately, however, components having high dielectric anisotropy lead mainly to an increased conductivity in mixtures because of their improved solubility capacity for ionic impurities. Therefore, components which have a dielectric anisotropy which is as high as possible with at the same time a conductivity which is as low as possible are sought after.

SUMMARY OF THE INVENTION

The present invention provides compounds of the general formula

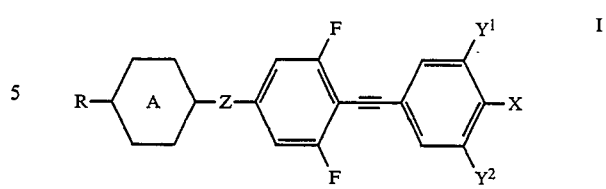

wherein
ring A represents 1,4-phenylene, pyridine-2,5-diyl, pyrimidine-2,5-diyl, trans-1,4-cyclohexylene or trans-1,3-dioxane-2,5-diyl;

Z signifies a single covalent bond, $-CH_2CH_2-$, $-OCH_2-$, $-CH_2O-$, $-(CH_2)_4-$, $-O(CH_2)_3-$, $-(CH_2)_3O-$ or, where ring A represents a saturated ring, also the trans form of $-CH=CH(CH_2)_2-$ or $-CH=CHCH_2O-$;

X signifies fluorine, chlorine, cyano, $-CF_3$, $-OCF_3$, $-OCHF_2$, alkyl, alkoxy or alkoxyalkyl with 1 to 6 carbon atoms;

$Y^1$, $Y^2$ each independently signify fluorine or hydrogen; and

R signifies alkyl, alkoxy, alkenyl or alkenyloxy with 1 or, respectively, 2 to 12 carbon atoms in which one $CH_2$ group or two non-adjacent $CH_2$ groups can be replaced by oxygen and/or one or more hydrogen atoms can be replaced by fluorine atoms.

The compounds in accordance with the invention are liquid crystals having a pronounced nematic phase and high optical and dielectric anisotropy with a relatively low rotation viscosity and lead to comparatively low threshold potentials and short response times. The conductivity is relatively low in spite of the high dielectric anisotropy. Moreover, in spite of multiple lateral substitution the clearing point is surprisingly high with a comparatively low melting point and small melting enthalpy. The relatively high optical anisotropy can be lowered or increased further according to desire by suitable choice of a saturated or aromatic ring for A.

The compounds in accordance with the invention have a very good solubility in mixtures and in wide concentration ranges. They are especially suitable for use in mixtures which are required to have in the case of low threshold potential a low conductivity and at the same time a comparatively high optical anisotropy, for example for TN, STN or TFT cells with a small layer thickness or with especially high contrast as are required, for example, for projection displays.

The term "saturated ring" embraces in the scope of the present invention trans-1,4-cyclohexylene or trans-1,3-dioxane-2,5-diyl.

In the compounds I in which A signifies a heterocyclic ring such as pyridine-2,5-diyl, pyrimidine-2,5-diyl or trans-1,3-dioxane-2,5-diyl the hetero atoms in the ring are always arranged such that they are in a position adjacent to the point of linkage with Z.

The bridging member Z preferably signifies a single covalent bond, $-CH_2CH_2-$, $-OCH_2-$ or $-CH_2O-$, but preferably a single covalent bond or $-CH_2CH_2-$.

DESCRIPTION OF THE PREFERRED EMBODIMENTS

Preferred sub-groups of compounds of formula I are therefore the compounds of the general formulae

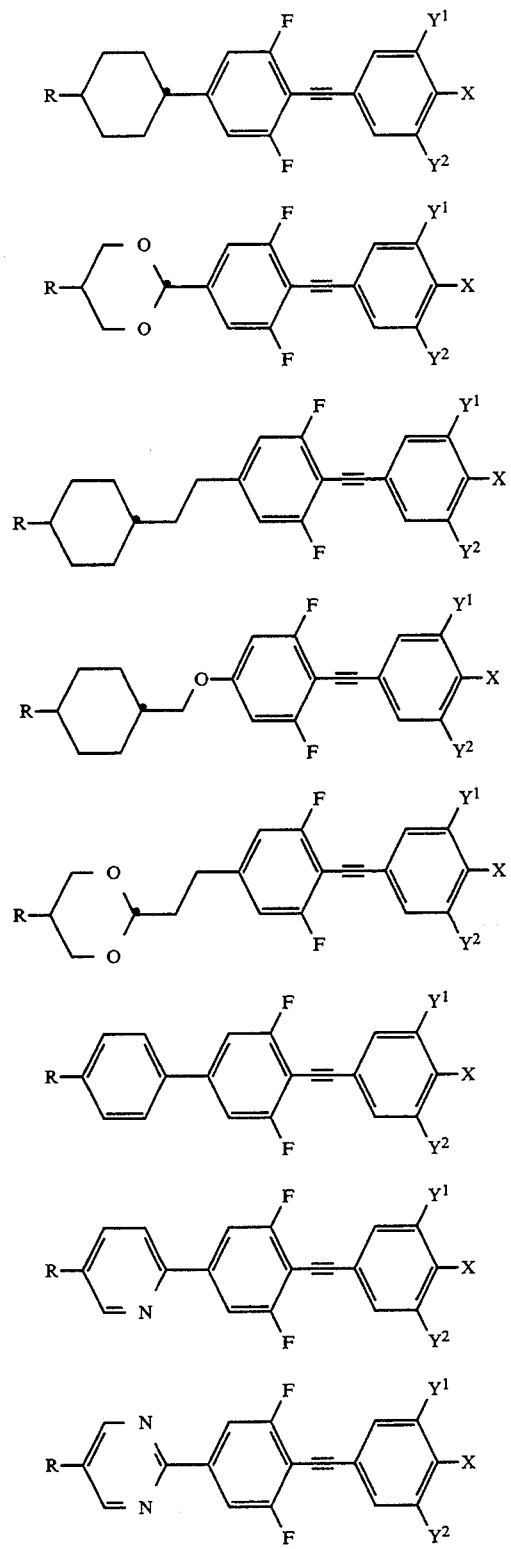

wherein R, X, $Y^1$ and $Y^2$ have the significances defined in formula I.

The residue R in formulae I and I-1 to I-8 can have 1 and, respectively, 2 to 12, preferably 1 and, respectively, 2 to 6, carbon atoms. It can in principle be straight-chain or branched, but is preferably straight-chain. When R signifies alkenyl, double bonds at C(1) or C(3) with the E-configuration or terminal double bonds are preferred and in the case of compounds having an aromatic ring A those at C(3) or terminally are preferred. When R signifies alkenyloxy, the preferred compounds are those having a double bond at C(2) with an E-configuration or those having a terminal double bond. If desired, the residue R can also have 1 to 2 oxygen atoms and/or one or more fluorine substituents. In this case, residues R having only one oxygen atom as well as those without fluorine substituents are preferred. Especially preferred residues R are accordingly methyl, ethyl, propyl, butyl, pentyl, hexyl, methoxy, ethoxy, propyloxy, butyloxy, pentyloxy, vinyl, 1-(E)-propenyl, 1-(E)-butenyl, 1-(E)-pentenyl, 1-(E)-hexenyl, 3-butenyl, 3-(E)-pentenyl, 3-(E)-hexenyl, 4-pentenyl, allyloxy, 2-(E)-butenyloxy, 3-butenyloxy, methoxymethyl, ethoxymethyl, propyloxymethyl, allyloxymethyl, methoxyethyl, ethoxyethyl, propyloxyethyl, methoxypropyl, ethoxypropyl, methoxy- 1E-propenyl, ethoxy- 1E-propenyl and the like.

In the compounds of general formulae I-1 to I-8 in which X signifies alkyl, alkoxy or alkoxyalkyl there are preferred straight-chain residues with 1 to 6 carbon atoms, with residues having 1 to 3 carbon atoms, such as, for example, methyl, ethyl, propyl, methoxy, ethoxy, propyloxy, methoxymethyl, ethoxymethyl or methoxyethyl, being especially preferred.

The substituents $Y^1$ and $Y^2$ defined in formulae I and I-1 to I-8 are in principle different from each other. However, those compounds in which one of the substituents $Y^1$ and $Y^2$ stands for hydrogen and the other stands for fluorine or hydrogen are preferred.

The manufacture of the compounds of formula I is presented in Scheme I in which the symbols given in formulae I-III have the aforementioned significance. The halogenation of the compounds IIa to III is preferably carried out in an inert solvent (e.g. tetrahydrofuran, ether, dimethoxyethane) at a low temperature (e.g. −70°). The reaction also takes place with bromine and leads to the analogous bromides which can likewise be used in the subsequent reaction to I.

Metal-catalyzed couplings of phenyl compounds with acetylenes, as is shown in the last step for the preparation of I from III, are basically known from the literature. As already mentioned, they can be carried out with bromides and iodides, as well as in some cases also with trifluorosulphonates and chlorides. Thereby, the mono-coupled acetylene is usually isolated, the protecting group, in this case isopropyloxy, is cleaved off and in a subsequent step the second phenyl ring is coupled. We have, however, found that the reaction of intermediates of formula III to compounds of formula I can also be realized in one step, i.e. without intervening working-up. Thereby, a compound of formula III is firstly reacted with 2-methyl-3-butyn-2-ol in an inert solvent, such as, for example, tetrahydrofuran, with catalytic amounts of bis-triphenylphosphine-palladium chloride, copper-I iodide and triphenylphosphine in the presence of triethylamine at an elevated temperature. Thereafter, potassium hydroxide and tetrabutylammonium hydrogen sulphate as well as the compound of type IIb are added and left to react at a higher temperature until the reaction has finished. In the case of compounds of type IIb analogous iodides, trifluorosulphonates and homologous polyfluoroalkylsulphonates, can basically also be used in place of bromides.

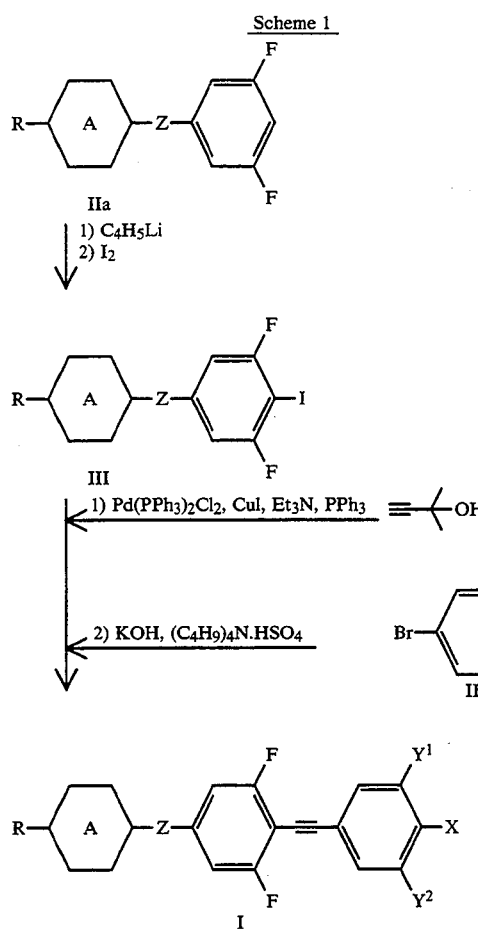

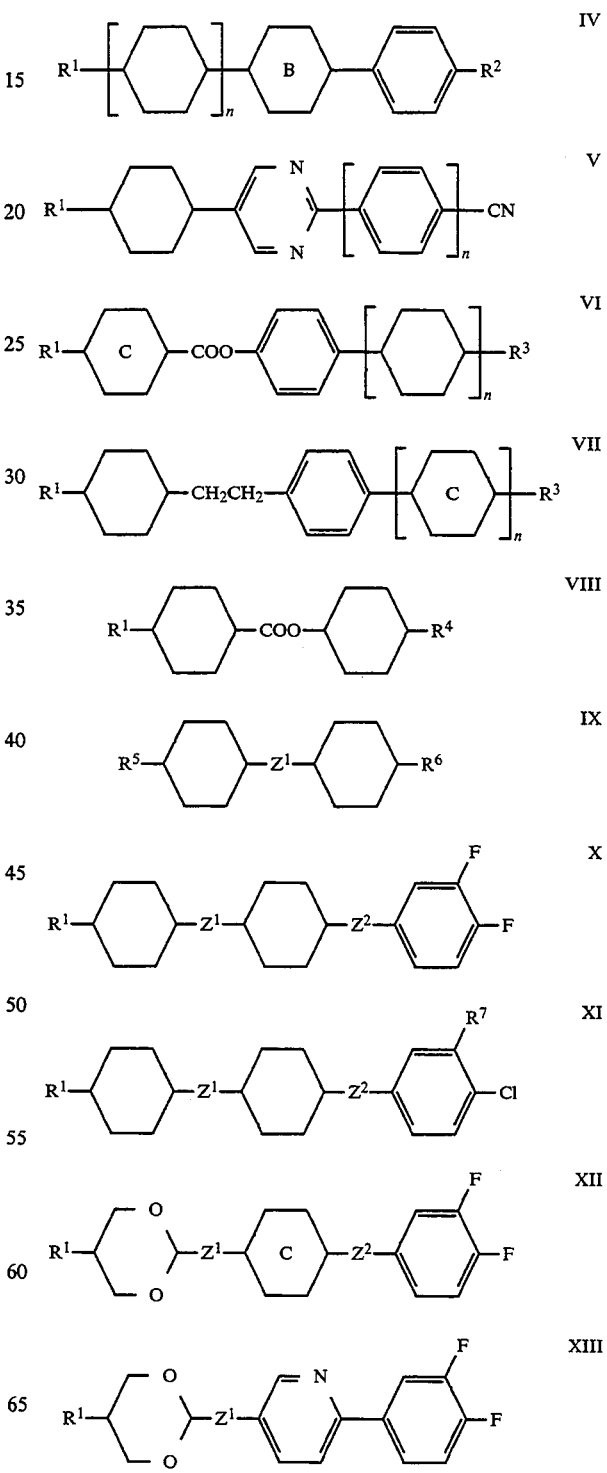

The starting materials of formula IIa are known or are analogues of known compounds and can be prepared according to known methods. Such compounds have already been described as intermediates for liquid crystals. Moreover, their synthesis is effected in complete analogy to the isomeric 3,4-difluorphenyl compounds, which will be familiar as liquid crystals to a person skilled in the art. Suitable substituted phenyl derivatives of formula IIb are commercially available in many instances or can be modified readily from marketed precursors according to methods known to a person skilled in the art.

The liquid crystalline mixtures in accordance with the invention contain at least two components of which at least one component is a compound of formula I. A second component and optionally additional components can be further compounds of formula I and/or other liquid crystal components.

The compounds of formula I are especially suitable for nematic mixtures or, insofar as at least one component of the mixture is optically active, also for cholesteric mixtures. A preferred field of application is the use as dielectrics in liquid crystal indicating devices having a twisted nematic liquid crystal structure such as TN cells, STN cells, SBE cells, OMI cells and TFT cells. Preferred mixtures are therefore those which contain one or more compounds having a positive dielectric anisotropy.

Having regard to the good solubility of the compounds of formula I in other liquid crystal materials and having regard to their good miscibility with one another, the content of the compounds of formula I in the mixtures in accordance with the invention can be relatively high and can be, for example, about 1–70 wt. %. In general, a content of about 3–40 wt. %, especially 5–30 wt. %, of compounds of formula I is preferred.

The mixtures in accordance with the invention preferably contain, in addition to one or more compounds of formula I, one or more compounds from the group of compounds of the general formulae

R¹—⌬—Z¹—⌬B—Z²—⌬C—⌬—R⁴  XIV

R¹—⌬—Z¹—⌬(R⁷)—Cl  XV

R¹—⌬—Z¹—⌬(F)—F  XVI

R¹—[dioxane]—Z¹—⌬(F)—F  XVII

R¹—[dioxane]—Z¹—⌬(R⁷)—Cl  XVIII

R¹—[pyrimidine]—⌬(F)—F  XIX

R¹—⌬—⌬(CN)(R⁵)  XX

R⁵—⌬—⌬—COO—⌬(R⁷)—R⁸  XXI

R¹—⌬—Z¹—⌬—⌬(R⁹)—R¹⁰  XXII wherein
R¹, R⁴ signify alkyl, alkoxyalkyl, 3E-alkenyl, 4-alkenyl or on saturated rings also 1E-alkenyl;

n signifies 0 or 1;

ring B denotes 1,4-phenylene, pyridine-2,5-diyl, pyrimidine-2,5-diyl, trans-1,4-cyclohexylene or trans-1,3-dioxane-2,5-diyl;

R² represents cyano, isothiocyanato, fluorine, alkyl, 3E-alkenyl, 4-alkenyl, alkoxy, 2E-alkenyloxy, 3-alkenyloxy or 1-alkynyl;

ring C signifies 1,4-phenylene or trans-1,4-cyclohexylene;

R³ denotes alkyl, 3E-alkenyl, 4-alkenyl, or on trans-1,4-cyclohexylene also 1E-alkenyl, or on 1,4-phenylene also cyano, isothiocyanato, alkoxy, 2E-alkenyloxy or 3-alkenyloxy;

R⁵ signifies alkyl, 1E-alkenyl, 3E-alkenyl or 4-alkenyl;

R⁶ represents cyano, alkyl, 1E-alkenyl, 3E-alkenyl, 4-alkenyl, alkoxy, 2E-alkenyloxy, 3-alkenyloxy, alkoxymethyl or (2E-alkenyl)oxymethyl;

Z¹, Z² each independently denote a single covalent bond or —CH₂CH₂—, with two aromatic rings always being linked by a single covalent bond;

R⁷ signifies hydrogen, fluorine or chlorine;

R⁸ represents cyano, fluorine or chlorine;

R⁹ denotes hydrogen or fluorine; and

R¹⁰ represents fluorine or chlorine.

The above term "saturated ring" embraces trans-1,4-cyclohexylene and trans-1,3-dioxane-2,5-diyl. The residues R¹ to R⁶ each preferably have 1 to 12 carbon atoms, particularly 1 to 7 carbon atoms. Straight-chain residues are generally preferred.

The term "alkyl" signifies in this connection preferably straight-chain residues with 1 to 12 carbon atoms, particularly with 1 to 7 carbon atoms such as, for example, methyl, ethyl, propyl, butyl, pentyl, hexyl or heptyl.

The term "alkyloxyalkyl" signifies in this connection preferably straight-chain residues with 1 to 12 carbon atoms, particularly with 1 to 7 carbon atoms, such as, for example, methoxymethyl, ethoxymethyl, propyloxymethyl, butyloxymethyl, methoxypropyl and the like.

The term "alkyloxy" signifies in this connection preferably straight-chain residues with 1 to 12 carbon atoms, particularly with 1 to 7 carbon atoms, such as, for example, methoxy, ethoxy, propyloxy, butyloxy, pentyloxy, hexyloxy, heptyloxy and the like.

The term "1E-alkenyl" signifies in this connection preferably straight-chain alkenyl residues with 2 to 12, particularly with 2 to 7, carbon atoms in which the double bond is situated in the 1-position, such as, for example, vinyl, 1E-propenyl, 1E-butenyl, 1E-pentenyl, 1E-hexenyl, 1E-heptenyl and the like.

The term "3E-alkenyl" signifies in this connection preferably straight-chain alkenyl residues with 4 to 12, particularly with 4 to 7, carbon atoms in which the double bond is situated in the 3-position, such as, for example, 3-butenyl, 3E-pentenyl, 3E-hexenyl, 3E-heptenyl and the like.

The term "4-alkenyl" signifies in this connection preferably straight-chain alkenyl residues with 5 to 12 carbon atoms in which the double bond is situated in the 4-position, such as, for example, 4-pentenyl, 4-hexenyl, 4-heptenyl and the like.

The term "2E-or 3Z-alkenyloxy" signifies in this connection preferably straight-chain alkenyl residues with 3 and, respectively 4 to 12 carbon atoms, particularly with 3 and, respectively 4 to 7 carbon atoms in which the double bond is situated in the 2- and, respectively, 3-position and E and, respectively, Z indicates the preferred configuration, such as, for example, allyloxy, 2E-butenyloxy, 2E-pentenyloxy, 2E-hexenyloxy, 2E-heptenyloxy, 3-butenyloxy, 3Z-pentenyloxy, 3Z-hexenyloxy, 3Z-heptenyloxy, 4-pentenyloxy, 5-hexenyloxy, 6-heptenyloxy and the like.

The term "1-alkynyl" signifies in this connection preferably straight-chain alkynyl residues with 2 to 12, particularly with 2 to 7, carbon atoms in which the triple bond is situated in the 1-position, such as, for example, ethynyl, 1-propynyl, 1-butynyl, 1-pentynyl and the like.

The manufacture of the liquid crystalline mixtures and of the electro-optical devices can be effected in a manner known per se.

The invention is illustrated in more detail by the following Examples. In the Examples C signifies a crystalline phase, N signifies a nematic phase, S signifies a smectic phase and I signifies the isotropic phase. $V_{10}$ denotes the voltage for 10% transmission. $t_{on}$ and $t_{off}$ denote respectively the switching-on time and the switching-off time. $\Delta n$ denotes the optical anisotropy.

EXAMPLE 1 a) 5.9 ml of a 1.6N butyllithium solution in hexane were added dropwise during 20 min. to a solution of 2.14 g of 1-(trans-4-propylcyclohexyl)-3,5-difluorobenzene in 20 ml of dry detrahydrofuran at −70° C. and the mixture was left to react at −70° C. for 1 hr. Then, a solution of 2.4 g of iodine in 10 ml of dry tetrahydrofuran was added dropwise at −60° C. within 10 min. and the mixture was gradually warmed to room temperature during a further 30 min. The yellow solution obtained was treated with 10 ml of water and then with 10 ml of a 10 percent aqueous sodium bicarbonate solution extracted with ether. The ether solution was washed with sat. sodium chloride solution and several times with water, dried over magnesium sulphate, filtered and concentrated. Chromatography of the residue over 150 g of silica gel with hexane gave 3.27 g of 1-(trans-4-propylcyclohexyl)-3,5-difluoro-4-iodobenzene as a colourless liquid.

b) A mixture of 1 g of 1-(trans-4-propylcyclohexyl)-3,5-difluoro-4-iodobenzene, 0.294 g of 2-methyl-3-butyn-2-ol, 0.077 g of bis(triphenylphosphine)palladium dichloride, 0.842 g of triethylamine, 0.084 g of triphenylphosphine and 10 ml of tetrahydrofuran was held under reflux for 48 hrs. Then, 0.326 ml of 1-bromo-3,4-difluorobenzene, 0.493 g of powdered potassium hydroxide and 0.205 g of tetrabutylammonium hydrogen sulphate were added in this sequence and the mixture was left to react under reflux for 16 hrs. Thereupon, the reaction mixture was cooled, poured into 25 ml of 1N sulphuric acid and extracted with ether. The ether phase was washed several times with sat. sodium chloride solution, dried over magnesium sulphate and evaporated on a rotary evaporator. Chromatography of the residue on 170 g of silica gel with hexane and subsequent crystallization from methanol gave 0.53 g of 4-(trans-4-propylcyclohexyl)-2,6,3',4'-tetrafluorotolane. M.p. (C/N) 71.3° C., cl.p. (N/I) 126° C.

The following compounds can be manufactured in an analogous manner:

4-(trans-4-Ethylcyclohexyl)-2,6,3',4'-tetrafluorotolane;
4-(trans-4-butylcyclohexyl)-2,6,3',4'-tetrafluorotolane;
4-(trans-4-pentylcyclohexyl)-2,6,3',4'-tetrafluorotolane;
4-(trans-4-vinylcyclohexyl)-2,6,3',4'-tetrafluorotolane;
4-[trans-4-(1E-propenyl)cyclohexyl]-2,6,3',4'-tetrafluorotolane;
4-[trans-4-(3-butenyl)cyclohexyl]-2,6,3',4'-tetrafluorotolane;
4-[trans-4-(3-methoxy-1E-propenyl)cyclohexyl]-2,6,3',4'-tetrafluorotolane;
4-[trans-4-(3-methoxypropyl)cyclohexyl]-2,6,3',4'-tetrafluorotolane;
4-(trans-4-propylcyclohexyl)-2,6,4'-trifluorotolane;
4-(trans-4-propylcyclohexyl)-2,6-difluoro-4'-chlorotolane, m.p. (C/N) 100.4° C., cl.p. (N/I) 188.8° C.;
4-(trans-4-vinylcyclohexyl)-2,6-difluoro-4'-chlorotolane;
4-[trans-4-(3-methoxypropyl)cyclohexyl]-2,6-difluoro-4'-chlorotolane;
4-(trans-4-propylcyclohexyl)-2,6,3'-trifluoro-4'-chlorotolane; m.p. (C/N) 90°, cl.p. (N/I) 158.9°;
4-[trans-4-(1E-propenyl)cyclohexyl]-2,6,3'-trifluoro-4'-chlorotolane;
4-[trans-4-(3-methoxypropyl)cyclohexyl]-2,6,3'-trifluoro-4'-chlorotolane;
4-(trans-4-propylcyclohexyl)-2,6,3'-trifluoro-4'-cyanotolane, m.p. (C/N) 134.8° C., cl.p. (N/I) 211.8° C.;
4-(trans-4-propylcyclohexyl)-2,6,3'-trifluoro-4'-trifluoromethyltolane;
4-(trans-4-propylcyclohexyl)-2,6-difluoro-4'-trifluoromethoxytolane, m.p. (C/S) 56° C., (S/N) 84.5° C., cl.p. (N/I) 169.4° C.;
4-(trans-4-propylcyclohexyl)-2,6,3'-trifluoro-4'-trifluoromethoxytolane;
4-(trans-4-propylcyclohexyl)-2,6-difluoro-4'-difluoromethoxytolane, m.p. (C/N) 80.5° C., cl.p. (N/I) 181.2° C.;
4-(trans-4-propylcyclohexyl)-2,6,3'-trifluoro-4'-difluoromethoxytolane, m.p. (C/N) 47.5° C., cl.p (N/I) 155.6° C.;
4-(trans-5-propyl-1,3-dioxan-2-yl)-2,6,3',4'-tetrafluorotolane;
4-(trans-5-butyl-1,3-dioxan-2-yl)-2,6,3',4'-tetrafluorotolane;
4-(trans-5-pentyl-1,3-dioxan-2-yl)-2,6,3',4'-tetrafluorotolane;
4-[trans-5-(1E-propenyl)-1,3-dioxan-2-yl]-2,6,3',4'-tetrafluorotolane, m.p. (C/N) 99.4° C., cl.p. (N/I) 151.9° C.;
4-[trans-5-(3-butenyl)-1,3-dioxan-2-yl]-2,6,3',4'-tetrafluorotolane;
4-[trans-5-(3-methoxy-1E-propenyl)-1,3-dioxan-2-yl]-2,6,3',4'-tetrafluorotolane;
4-[trans-5-(3-methoxypropyl)-1,3-dioxan-2-yl]-2,6,3',4'-tetrafluorotolane;
4-(trans-5-propyl-1,3-dioxan-2-yl)-2,6,4'-trifluorotolane;
4-(trans-5-propyl-1,3-dioxan-2-yl)-2,6-difluoro-4'-chlorotolane;
4-[trans-5-(3-methoxypropyl)-1,3-dioxan-2-yl]-2,6-difluoro-4'-chlorotolane;
4-(trans-5-propyl-1,3-dioxan-2-yl)-2,6,3'-trifluoro-4'-chlorotolane;
4-[trans-5-(1E-propenyl)-1,3-dioxan-2-yl]-2,6,3'-trifluoro-4'-chlorotolane, m.p. (C/N) 117° C., cl.p. (N/I) 184.4° C.;
4-[trans-5-(3-methoxypropyl)-1,3-dioxan-2-yl]-2,6,3'-trifluoro-4'-chlorotolane;
4-(trans-5-propyl-1,3-dioxan-2-yl)-2,6,3'-trifluoro-4'-cyanotolane;
4-[trans-5-(1E-propenyl)-1,3-dioxan-2-yl]-2,6,3'-trifluoro-4'-cyanotolane, m.p. (C/N) 156° C., cl.p. (N/I) >225° C.;
4-(trans-5-propyl-1,3-dioxan-2-yl)-2,6-difluoro-4'-ethyltolane;
4-(trans-5-propyl-1,3-dioxan-2-yl)-2,6-difluoro-4'-ethoxytolane;
4-(trans-5-propyl-1,3-dioxan-2-yl)-2,6,3'-trifluoro-4'-methyltolane;

4-(trans-5-propyl-1,3-dioxan-2-yl)-2,6,3'-trifluoro-4'-methoxytolane;
4-(trans-5-propyl-1,3-dioxan-2-yl)-2,6,3'-trifluoro-4'-methoxymethyltolane;
4-(trans-5-propyl-1,3-dioxan-2-yl)-2,6,3'-trifluoro-4'-trifluoromethyltolane;
4-(trans-5-propyl-1,3-dioxan-2-yl)-2,6,3'-trifluoro-4'-trifluoromethoxytolane;
4-(trans-5-propyl-1,3-dioxan-2-yl)-2,6,3'-trifluoro-4'-difluoromethoxytolane;
4-[2-(trans-4-propylcyclohexyl)ethyl]-2,6,3',4'-tetrafluorotolane;
4-[2-(trans-4-butylcyclohexyl)ethyl]-2,6,3',4'-tetrafluorotolane;
4-[2-(trans-4-pentylcyclohexyl)ethyl]-2,6,3',4'-tetrafluorotolane;
4-[2-(trans-4-vinylcyclohexyl)ethyl]-2,6,3',4'-tetrafluorotolane;
4-[2-[trans-4-(1E-propenyl)cyclohexyl]ethyl]-2,6,3',4'-tetrafluorotolane;
4-[2-[trans-4-(3-butenyl)cyclohexyl]ethyl]-2,6,3',4'-tetrafluorotolane;
4-[2-[trans-4-(3-methoxy-1E-propenyl)ethyl]cyclohexyl]-2,6,3',4'-tetrafluorotolane;
4-[2-[trans-4-(3-methoxypropyl)cyclohexyl]ethyl]-2,6,3',4'-tetrafluorotolane;
4-[2-(trans-4-propylcyclohexyl)ethyl]-2,6,4'-trifluorotolane;
4-[2-(trans-4-propylcyclohexyl)ethyl]-2,6-difluoro-4'-chlorotolane;
4-[2-(trans-4-vinylcyclohexyl)ethyl]-2,6-difluoro-4'-chlorotolane;
4-[2-[trans-4-(3-methoxypropyl)cyclohexyl]ethyl]-2,6-difluoro-4'-chlorotolane;
4-[2-(trans-4-propylcyclohexyl)ethyl]-2,6,3'-trifluoro-4'-chlorotolane;
4-[2-[trans-4-(1E-propenyl)cyclohexyl]ethyl]-2,6,3'-trifluoro-4'-chlorotolane;
4-[2-[trans-4-(3-methoxypropyl)cyclohexyl]ethyl]-2,6,3'-trifluoro-4'-chlorotolane;
4-[2-(trans-4-propylcyclohexyl)ethyl]-2,6,3'-trifluoro-4'-cyanotolane;
4-[2-(trans-4-propylcyclohexyl)ethyl]-2,6,3'-trifluoro-4'-trifluoromethyltolane;
4-[2-(trans-4-propylcyclohexyl)ethyl]-2,6,3'-trifluoro-4'-trifloromethoxytolane;
4-[2-(trans-4-propylcyclohexyl)ethyl]-2,6,3'-trifluoro-4'-difluoromethoxytolane;
4-[(trans-4-propylcyclohexyl)methoxy]-2,6,3',4'-tetrafluorotolane;
4-[(trans-4-propylcyclohexyl)methoxy]-2,6,3'-trifluoro-4'-chlorotolane;
4-[2-(trans-5-propyl-1,3-dioxan-2-yl)ethyl]-2,6,3',4'-tetrafluorotolane;
4-[2-[trans-5-(1E-propenyl)-1,3-dioxan-2-yl)ethyl]-2,6,3',4'-tetrafluorotolane;
4-[2-(trans-5-(3-methoxypropyl)-1,3-dioxan-2-yl)ethyl]-2,6,3 ',4'-tetrafluorotolane;
4-[2-(trans-5-propyl-1,3-dioxan-2yl)ethyl]-2,6,3'-trifluoro-4'-chlorotolane;
4-(4-ethylphenyl)-2,6,3',4'-tetrafluorotolane;
4-(4-propylphenyl)-2,6,3',4'-tetrafluorotolane, m.p. (C/I) 90° C.;
4-(4-butylphenyl)-2,6,3',4'-tetrafluorotolane;
4-(4-pentylphenyl)-2,6,3',4'-tetrafluorotolane;
4-(4-hexylphenyl)-2,6,3',4'-tetrafluorotolane;
4-(4-heptylphenyl)-2,6,3',4'-tetrafluorotolane;
4-[4-(3-butenyl)phenyl]-2,6,3',4'-tetrafluorotolane;
4-[4-(3E-pentenyl)phenyl]-2,6,3',4'-tetrafluorotolane;
4-(4-ethoxyphenyl)-2,6,3',4'-tetrafluorotolane;
4-(4-propyloxyphenyl)-2,6,3',4'-tetrafluorotolane;
4-(4-butyloxyphenyl)-2,6,3',4'-tetrafluorotolane;
4-(4-pentyloxyhenyl)-2,6,3',4'-tetrafluorotolane;
4-(4-allyloxyhenyl)-2,6,3',4'-tetrafluorotolane;
4-[4-(3-methoxypropyl)phenyl]-2,6,3',4'-tetrafluorotolane;
4-(4-propylphenyl)-2,6,3'-trifluoro-4'-chlorotolane, m.p. (C/N) 92.3° C., cl.p. (N/I) 142.7° C.;
4-(4-propyloxyphenyl)-2,6,3'-trifluoro-4'-chlorotolane;
4-(4-propylphenyl)-2,6,3'-trifluoro-4'-cyanotolane;
4-(4-propylphenyl)-2,6,3'-trifluoro-4'-trifluoromethyltolane;
4-(4-propylphenyl)-2,6,3'-trifluoro-4'-trifluoromethoxytolane;
4-(4-propylphenyl)-2,6,3'-trifluoro-4'-difluoromethoxytolane;
4-(5-ethylpyridin-2-yl)-2,6,3',4'-tetrafluorotolane;
4-(5-propylpyridin-2-yl)-2,6,3',4'-tetrafluorotolane, m.p. (C/N) 101.1° C., cl.p. (N/I) 131.7° C.;
4-(5-butylpyridin-2-yl)-2,6,3',4'-tetrafluorotolane;
4-(5-pentylpyridin-2-yl)-2,6,3',4'-tetrafluorotolane;
4-(5-ethoxypyridin-2-yl)-2,6,3',4'-tetrafluorotolane;
4-(5-propyloxypyridin-2-yl)-2,6,3',4'-tetrafluorotolane;
4-(5-allyloxypyridin-2-yl)-2,6,3',4'-tetrafluorotolane;
4-[5-(3-methoxypropyl)pyridin-2-yl]-2,6,3',4'-tetrafluorotolane;
4-(5-propylpyridin-2-yl)-2,6,3'-trifluoro-4'-chlorotolane, m.p. (C/N) 113.4° C., cl.p. (N/I) 161.7° C.;
4-(5-butylpyridin-2-yl)-2,6,3'-trifluoro-4'-chlorotolane;
4-(5-pentylpyridin-2-yl)-2,6,3'-trifluoro-4'-chlorotolane;
4-(5-(3-methoxypropyl)pyridin-2-yl)-2,6,3'-trifluoro-4'-chlorotolane;
4-(5-ethylpyrimidin-2-yl)-2,6,3',4'-tetrafluorotolane;
4-(5-propylpyrimidin-2-yl)-2,6,3',4'-tetrafluorotolane, m.p. (C/N) 144.6° C., cl.p. (N/I) 154° C.;
4-(5-butylpyrimidin-2-yl)-2,6,3',4'-tetrafluorotolane;
4-(5-pentylpyrimidin-2-yl)-2,6,3',4'-tetrafluorotolane;
4-(5-ethoxypyrimidin-2-yl)-2,6,3',4'-tetrafluorotolane;
4-(5-propyloxypyrimidin-2-yl)-2,6,3',4'-tetrafluorotolane;
4-(5-allyloxypyrimidin-2-yl)-2,6,3',4'-tetrafluorotolane;
4-[5-(3-methoxypropyl)pyrimidine-2-yl]-2,6,3',4'-tetrafluorotolane;
4-(5-propylpyrimidin-2-yl)-2,6,3'-trifluoro-4'-chlorotolane, m.p. (C/N) 160.3° C., cl.p. (N/I) 176.5° C.;
4-(5-butylpyrimidin-2-yl)-2,6,3'-trifluoro-4'-chlorotolane;
4-(5-pentylpyrimidin-2-yl)-2,6,3'-trifluoro-4'-chlorotolane;
4-(5-allyloxypyrimidin-2-yl)-2,6,3'-trifluoro-4'-chlorotolane;
4-(5-(3-methoxypropyl)pyrimidin-2-yl)-2,6,3'-trifluoro-4'-chlorotolane.

EXAMPLE 2

Binary mixtures (BM) with 4-(trans-4-pentylcyclohexyl)benzonitrile were prepared in order to investigate the properties of the compounds of formula I in mixtures. The threshold potential and the response times were measured at 22° C. in a TN cell (low bias tilt)

having a plate separation of 8 mm; the 2.5-fold value of the threshold potential ($V_{10}$) being chosen as the operating voltage. The corresponding data for 4-(trans-4-pentylcyclohexyl)benzonitrile are: cl.p.. (N/I)=54.6° C., $V_{10}$=1.62 $V_{10}$, $t_{on}$=22 ms, $t_{off}$=42 ms, $\Delta n$=0.120.

BM-1

90 wt. % of 4-(trans-4-pentylcyclohexyl)benzonitrile
10 wt. % of 4-(trans-4-propylcyclohexyl)-2,6,3',4'-tetrafluorotolane
cl.p. (N/I): 57.3° C., $V_{10}$=1,57 V, $t_{on}$=26 ms, $t_{off}$=43 ms, $\Delta n$=0.129.

BM-2

80 wt. % of 4-(trans-4-pentylcyclohexyl)benzonitrile
20 wt. % of 4-(trans-4-propylcyclohexyl)-2,6,3',4'-tetrafluorotolane
cl.p. (N/I): 60.3° C., $V_{10}$=1.51 V, $t_{on}$=28 ms, $t_{off}$=47 ms, $\Delta n$=0.137.

BM-3

90 wt. % of 4-(trans-4-pentyl-cyclohexyl)benzonitrile
10 wt. % of 4-[trans-5-(1E-propenyl)-1,3-dioxan-2-yl]-2,6,3',4'-tetrafluorotolane;
cl.p. (N/I): 56.5° C., $V_{10}$=1.50 V, $t_{on}$=26 ms, $t_{off}$=43 ms, $\Delta n$=0.132.

BM-4

80 wt. % of 4-(trans-4-pentyl-cyclohexyl)benzonitrile
20 wt. % of 4-[trans-5-(1E-propenyl)-1,3-dioxan-2-yl]-2,6,3',4'-tetrafluorotolane;
cl.p. (N/I): 59.9° C., $V_{10}$=1.42 V, $t_{on}$=29 ms, $t_{off}$=49 ms, $\Delta n$=0.140.

BM-5

90 wt. % of 4-(trans-4-pentyl-cyclohexyl)benzonitrile
10 wt. % of 4-[trans-5-(1E-propenyl)-1,3-dioxan-2-yl]-2,6,3'-trifluoro-4'-chlorotolane;
cl.p. (N/I): 58.3° C., $V_{10}$=1.50 V, $t_{on}$=28 ms, $t_{off}$=43 ms, $\Delta n$=0.136.

BM-6

80 wt. % of 4-(trans-4-pentyl-cyclohexyl)benzonitrile
20 wt. % of 4-[trans-5-(1E-propenyl)-1,3-dioxan-2-yl]-2,6,3'-trifluoro-4'-chlorotolane;
cl.p. (N/I): 63.9° C., $V_{10}$=1.41 V, $t_{on}$=31 ms, $t_{off}$=47 ms.

BM-7

90 wt. % of 4-(trans-4-pentyl-cyclohexyl)benzonitrile
10 wt. % of 4-(4-propylphenyl)-2,6,3',4'-tetrafluorotolane;
cl.p. (N/I): 54.0° C., $V_{10}$=1.52 V, $t_{on}$=29 ms, $t_{off}$=44 ms, $\Delta n$=0.138.

BM-8

80 wt. % of 4-(trans-4-pentyl-cyclohexyl)benzonitrile
20 wt. % of 4-(4-propylphenyl)-2,6,3',4'-tetrafluorotolane;
cl.p. (N/I): 53.1° C., $V_{10}$=1.46 V, $t_{on}$=27 ms, $t_{off}$=45 ms, $\Delta n$=0.153.

BM-9

90 wt. % of 4-(trans-4-pentyl-cyclohexyl)benzonitrile
10 wt. % of 4-(4-propylphenyl)-2,6,3'-trifluoro-4'-chlorotolane;
cl.p. (N/I): 58.1° C., $V_{10}$=1.61 V, $t_{on}$=27 ms, $t_{off}$=42 ms, $\Delta n$=0.143.

BM-10

80 wt. % of 4-(trans-4-pentyl-cyclohexyl)benzonitrile
20 wt. % of 4-(4-propylphenyl)-2,6,3'-trifluoro-4'-chlorotolane;
cl.p. (N/I): 62.3° C., $V_{10}$=1.55 V, $t_{on}$=30 ms, $t_{off}$=47 ms, $\Delta n$=0.164.

BM-11

90 wt. % of 4-(trans-4-pentyl-cyclohexyl)benzonitrile
10 wt. % of 4-(5-propylpyridin-2-yl)-2,6,3',4'-tetrafluorotolane;
cl.p. (N/I): 56.1° C., $V_{10}$=1.40 V, $t_{on}$=28 ms, $t_{off}$=45 ms, $\Delta n$=0.138.

BM-12

80 wt. % of 4-(trans-4-pentyl-cyclohexyl)benzonitrile
20 wt. % of 4-(5-propylpyridin-2-yl)-2,6,3',4'-tetrafluorotolane;
cl.p. (N/I): 58.3° C., $V_{10}$=1.29 V, $t_{on}$=35 ms, $t_{off}$=51 ms, $\Delta n$=0.155.

BM-13

90 wt. % of 4-(trans-4-pentyl-cyclohexyl)benzonitrile
10 wt. % of 4-(5-propylpyridin-2-yl)-2,6,3'-trifluoro-4'-chloro tolane;
cl.p. (N/I): 57.8° C., $V_{10}$=1.49 V, $t_{on}$=27 ms, $t_{off}$=45 ms, $\Delta n$=0.146.

BM-14

80 wt. % of 4-(trans-4-pentyl-cyclohexyl)benzonitrile
20 wt. % of 4-(5-propylpyridin-2-yl)-2,6,3'-trifluoro-4'-chlorotolane;
cl.p. (N/I): 63.0° C., $V_{10}$=1.39 V, $t_{on}$=32 ms, $t_{off}$=52 ms, $\Delta n$=0.162.

BM-15

90 wt. % of 4-(trans-4-pentyl-cyclohexyl)benzonitrile
10 wt. % of 4-(5-propylpyrimidin-2-yl)-2,6,3',4'-tetrafluorotolane;
cl.p. (N/I): 56.8° C., $V_{10}$=1.42 V, $t_{on}$=26 ms, $t_{off}$=43 ms, $\Delta n$=0.126.

BM-16

80 wt. % of 4-(trans-4-pentyl-cyclohexyl)benzonitrile
20 wt. % of 4-(5-propylpyrimidin-2-yl)-2,6,3',4'-tetrafluorotolane;
cl.p. (N/I): 57.6° C., $V_{10}$=1.39 V, $t_{on}$=27 ms, $t_{off}$=47 ms.

BM-17

90 wt. % of 4-(trans-4-pentyl-cyclohexyl)benzonitrile
10 wt. % of 4-(trans-4-propylcyclohexyl)-2,6-difluoro-4'-trifluoromethoxytolane;
cl.p. (N/I): 58.7° C., $V_{10}$=1.53 V, $t_{on}$=27 ms, $t_{off}$=44 ms, $\Delta n$=0.130.

BM-18

80 wt. % of 4-(trans-4-pentyl-cyclohexyl)benzonitrile
20 wt. % of 4-(trans-4-propylcyclohexyl)-2,6-difluoro-4'-trifluoromethoxytolane;
cl.p. (N/I): 64.3° C., $V_{10}$=1.58 V, $t_{on}$=27 ms, $t_{off}$=46 ms, $\Delta n$=0.140.

BM-19

90 wt. % of 4-(trans-4-pentyl-cyclohexyl)benzonitrile
10 wt. % of 4-(trans-4-propylcyclohexyl)-2,6-difluoro-4'-difluoromethoxytolane;

cl.p. (N/I): 60.4° C., $V_{10}=1.52$ V, $t_{on}=25$ ms, $t_{off}=39$ ms, $\Delta n=0.133$.

BM-20

80 wt. % of 4-(trans-4-pentyl-cyclohexyl)benzonitrile 20 wt. % of 4-(trans-4-propylcyclohexyl)-2,6-difluoro-4'-difluoromethoxytolane;

cl.p. (N/I): 67.4° C., $V_{10}=1.48$ V, $t_{on}=32$ ms, $t_{off}=47$ ms, $\Delta n=0.144$.

BM-21

90 wt. % of 4-(trans-4-pentyl-cyclohexyl)benzonitrile 10 wt. % of 4-(trans-4-propylcyclohexyl)-2,6,3'-trifluoro-4'-difluoromethoxytolane;

cl.p. (N/I): 58.0° C., $V_{10}=1.43$ V, $t_{on}=30$ ms, $t_{off}=44$ ms, $\Delta n=0.130$.

BM-22

80 wt. % of 4-(trans-4-pentyl-cyclohexyl)benzonitrile 20 wt. % of 4-(trans-4-propylcyclohexyl)-2,6,3'-trifluoro-4'-difluoromethoxytolane;

cl.p. (N/I): 62.4° C., $V_{10}=1.41$ V, $t_{on}=34$ ms, $t_{off}=51$ ms, $\Delta n=0,139$.

We claim:

1. A compound of the formula

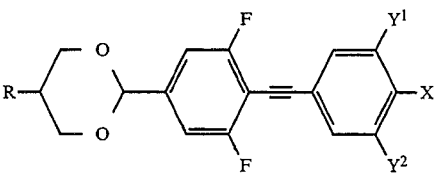

I-2 wherein R is 1E-propenyl; X is fluorine, chlorine, cyano, —CF3, —OCF3, —OCHF2, alkyl, alkoxy or alkoxylalkyl with 1 to 6 carbon atoms; and one of $Y^1$ and $Y^2$ is hydrogen and the other is hydrogen or fluorine.

2. A compound of claim 1 which is 4-[trans-5-(1E-propenyl)-1,3-dioxan-2-yl]-2,6,3',4'-tetrafluorotolane.

3. A compound of claim 1 which is 4-[trans-5-(1E-propenyl)-1,3-dioxan-2-yl]-2,6,3'-trifluoro-4'chlorotolane.

4. A compound of claim 1 which is 4-[trans-5-(1E-propenyl)-1,3-dioxan-2-yl]-2,6,3'-trifluoro-4'cyanotolane.

5. A liquid crystalline mixture containing at least two components, wherein at least one component is a compound of formula I defined in claim 1.

6. A liquid crystalline mixture in accordance with claim 5, wherein the content of compounds of formula I is 3–40 wt. %.

7. A liquid crystalline mixture in accordance with claim 1, wherein the content of compounds of formula I is 5–30 wt. %.

* * * * *